US009314355B2

(12) United States Patent
Styrc et al.

(10) Patent No.: US 9,314,355 B2
(45) Date of Patent: Apr. 19, 2016

(54) DEVICE FOR TREATING A BLOOD VESSEL AND A METHOD OF PREPARING THE DEVICE

(75) Inventors: Mikolaj Styrc, Kopstal (BE); Ning Wen, Chantilly (FR)

(73) Assignee: CORMOVE, Bornel (FR)

( * ) Notice: Subject to any disclaimer, the term of this patent is extended or adjusted under 35 U.S.C. 154(b) by 2456 days.

(21) Appl. No.: 11/002,121

(22) Filed: Dec. 3, 2004

(65) Prior Publication Data

US 2005/0119722 A1     Jun. 2, 2005

(30) Foreign Application Priority Data

Dec. 9, 2003   (FR) .................................... 03 14424

(51) Int. Cl.
*A61F 2/95*     (2013.01)
(52) U.S. Cl.
CPC ........... *A61F 2/95* (2013.01); *A61F 2002/9505* (2013.01); *A61F 2002/9511* (2013.01)
(58) Field of Classification Search
CPC ........................... A61F 2002/9511; A61F 2/95
USPC .............................................. 623/1.11, 1.12
See application file for complete search history.

(56) References Cited

U.S. PATENT DOCUMENTS

| | | | |
|---|---|---|---|
| 5,035,706 A * | 7/1991 | Giantureo et al. ............ 606/198 |
| 5,464,449 A | 11/1995 | Ryan et al. | |
| 5,948,017 A | 9/1999 | Taheri | |
| 6,106,549 A | 8/2000 | Taheri | |
| 6,302,891 B1 * | 10/2001 | Nadal ............................ 606/108 |
| 6,319,287 B1 | 11/2001 | Frimberger | |
| 6,398,802 B1 | 6/2002 | Yee | |
| 6,533,811 B1 | 3/2003 | Ryan et al. | |
| 6,733,521 B2 * | 5/2004 | Chobotov et al. ............ 623/1.12 |
| 6,740,111 B1 * | 5/2004 | Lauterjung ..................... 623/1.1 |
| 6,855,159 B1 * | 2/2005 | Tanner et al. ................. 623/1.11 |
| 7,022,132 B2 * | 4/2006 | Kocur ........................... 623/1.11 |
| 7,267,694 B2 * | 9/2007 | Levine et al. ................ 623/23.7 |
| 2002/0029076 A1 | 3/2002 | Yee | |
| 2002/0099432 A1 | 7/2002 | Yee | |
| 2002/0143387 A1 * | 10/2002 | Soetikno et al. ............. 623/1.15 |
| 2004/0049256 A1 | 3/2004 | Yee | |

FOREIGN PATENT DOCUMENTS

EP          0707462       4/1996

* cited by examiner

*Primary Examiner* — Katherine M Shi
*Assistant Examiner* — Michael Mendoza
(74) *Attorney, Agent, or Firm* — Wenderoth, Lind & Ponack, L.L.P.

(57) ABSTRACT

A device includes a tubular endoprosthesis (11) and a hollow prop (13) provided in the vicinity of a distal end with at least one transverse retaining opening (23A). The device includes a releasable retaining member (31). It also includes filamentary line (33A) which forms an eyelet (41) around the retaining member (31), and a tightening loop (43) around the endoprosthesis (11), and which includes traction means (45) extending the tightening loop (43). The traction means (45) extend at least as far as a control end in the vicinity of a proximal end of the prop (13) and can be moved relative to the prop (13) towards the distal end of the prop (13) to a position in which the endoprosthesis (11) is in an expanded state. The invention is applicable to releasing endoprostheses in a blood vessel.

26 Claims, 8 Drawing Sheets

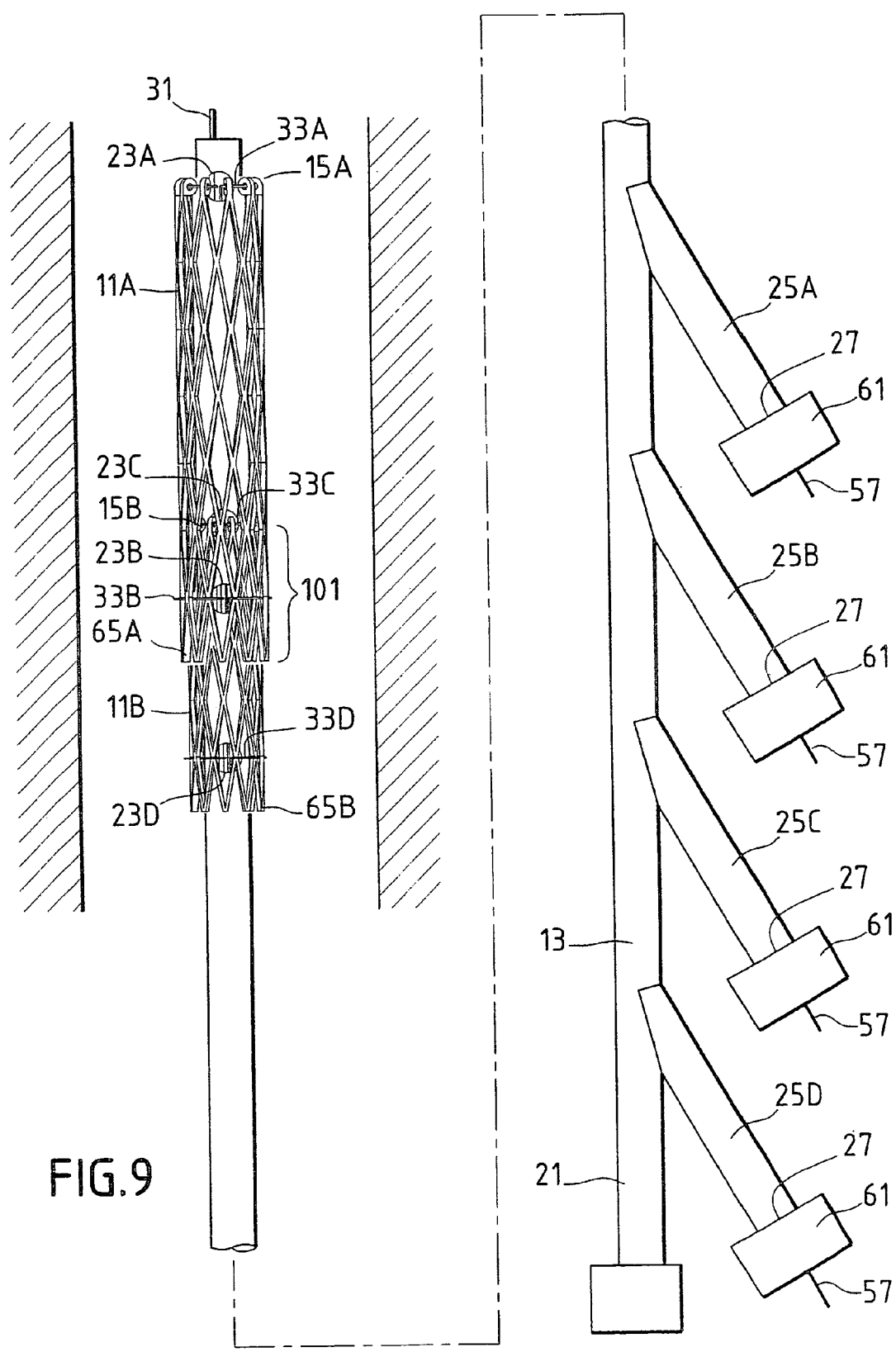

DEVICE FOR TREATING A BLOOD VESSEL AND A METHOD OF PREPARING THE DEVICE

BACKGROUND OF THE INVENTION

The present invention relates to a device for treating a blood vessel, the device being of the type comprising:
- at least one tubular endoprosthesis that is deployable between a retracted state and an expanded state;
- a hollow prop which extends longitudinally between a proximal end and a distal end, which prop is provided in the vicinity of its distal end with at least one transverse retaining opening;
- at least one releasable filamentary line forming at least one tightening loop which surrounds at least part of the endoproathesis, the tightening loop extending through the retaining opening to an eyelet and being engaged through a tightening opening formed transversely in the prop; the filamentary line further comprising traction means which extend the tightening loop from the tightening opening, the traction means extending inside the prop at least to a control end actuatable from the proximal end of the prop; and
- at least one releasable retaining member, the eyelet being engaged releasably on the retaining member.

Such a device is used for releasing tubular endoprostheses, commonly referred to as "stents", within a blood vessel.

A device of the above-specified type is described in EP-A-0 707 462. An endoprosthesis is mounted coaxially on two hollow props suitable for sliding relative to each other. The endoprosthesis is held in its retracted state using two filamentary lines binding its ends. The filamentary lines are engaged respectively in distal and proximal retaining openings formed respectively in each of the props.

To release the endoprosthesis, the props are moved to slide relative to each other so that the distance between the retaining openings decreases.

Reducing this distance causes the filamentary lines to relax and consequently causes simultaneously the two ends of the endoprosthesis to be deployed.

During deployment, the line holding the proximal end of the endoprosthesis moves towards the proximal end of the prop since the prop is moved towards the distal end of the endoprosthesis.

Nevertheless, such devices do not give full satisfaction. The device does not enable first one and then another one of the ends of the endoprosthesis to be deployed in succession, and in some cases that can lead to rather inaccurate positioning within the blood vessel.

SUMMARY OF THE INVENTION

An object of the invention is to propose a device for treating a blood vessel that can be positioned more accurately in the vessel.

To this end, the invention provides a device of the above-defined type for treating a blood vessel, characterized in that a traction means can be moved relative to a prop towards the distal end of the prop from a position under tension in which the endoprosthesis is in its retracted state, to a relaxed position in which the endoprosthesis is in its expanded state, at least in the vicinity of the tightening loop.

The device of the invention may include one or more of the following characteristics taken in isolation or in any technically feasible combination:
- the traction means are displaceable relative to the prop towards the proximal end of the prop from the relaxed position to the position under tension;
- a control passage is formed in the prop in the vicinity of its proximal end, the traction means comprising a portion projecting beyond the prop through the control passage, the length of the projecting portion when the endoprosthesis is in its retracted state being greater than the length of the projecting portion when the endoprosthesis is in the expanded state;
- the filamentary line comprises a single strand, the eyelet being deformable and being disposed at a distal end of the strand;
- the tightening opening and the retaining opening are distinct, and the device includes two filamentary lines forming two tightening loops engaged in the tightening and retaining openings, the tightening loops extending on either side of a longitudinal midplane of the prop;
- the retaining member comprises at least one retaining rod disposed to move inside the prop between a retaining position in which an active portion of the rod is in register with the retaining opening and the eyelet is engaged around the active portion, and a release position in which the active portion of the rod is spaced apart from the retaining opening, the rod including actuation means extending at least between the active portion and the proximal end of the prop in the retaining position;
- the device comprises a single prop having at least two retaining openings that are longitudinally offset, the distance between the retaining openings being constant, regardless of the state of the endoprosthesis;
- the longitudinal distance between the two retaining openings is substantially equal to the length of the endoprosthesis while in its retracted state, measured in a longitudinal direction of the endoprosthesis;
- the retaining openings extend on either side of a longitudinal midplane of the prop;
- the device includes a filamentary line for each retaining opening, each control end being engaged in a distinct control passage formed in the prop in the vicinity of its proximal end; and
- the device includes two endoprostheses that are longitudinally offset along the prop, each endoprosthesis being surrounded by at least one filamentary line associated with a retaining opening.

The invention also provides a method of preparing a device as described above, prior to being implanted in a blood vessel, the method being characterized in that it comprises the following steps:
a) the endoprosthesis is conserved in its expanded state; and then
b) the traction means are moved towards the proximal end of the prop so as to bring the endoprosthesis into its retracted state, for implantation purposes.

BRIEF DESCRIPTION OF THE DRAWINGS

Embodiments of the invention are described below with reference to the accompanying drawings, in which:

FIG. 9 is an elevation view of a fourth device of the invention.

DETAILED DESCRIPTION OF THE PREFERRED EMBODIMENTS

The device shown in FIGS. 1 to 6 comprises a tubular endoprosthesis 11 mounted coaxially on a single prop 13 and connected to said prop 13 by releasable retaining means.

The endoprosthesis 11 comprises a tubular trellis of stainless steel which possesses spring properties. Thus, the endoprosthesis is self-expanding.

In conventional manner, the endoprosthesis 11 is suitable for deforming spontaneously from a compressed state, in which it presents a small diameter (FIG. 1) to an expanded state in which it presents a larger diameter (FIG. 5), the expanded state constituting its rest state.

At a distal end 15 of the endoprosthesis, the trellis presents wires folded to form loops 17.

Figure 1:
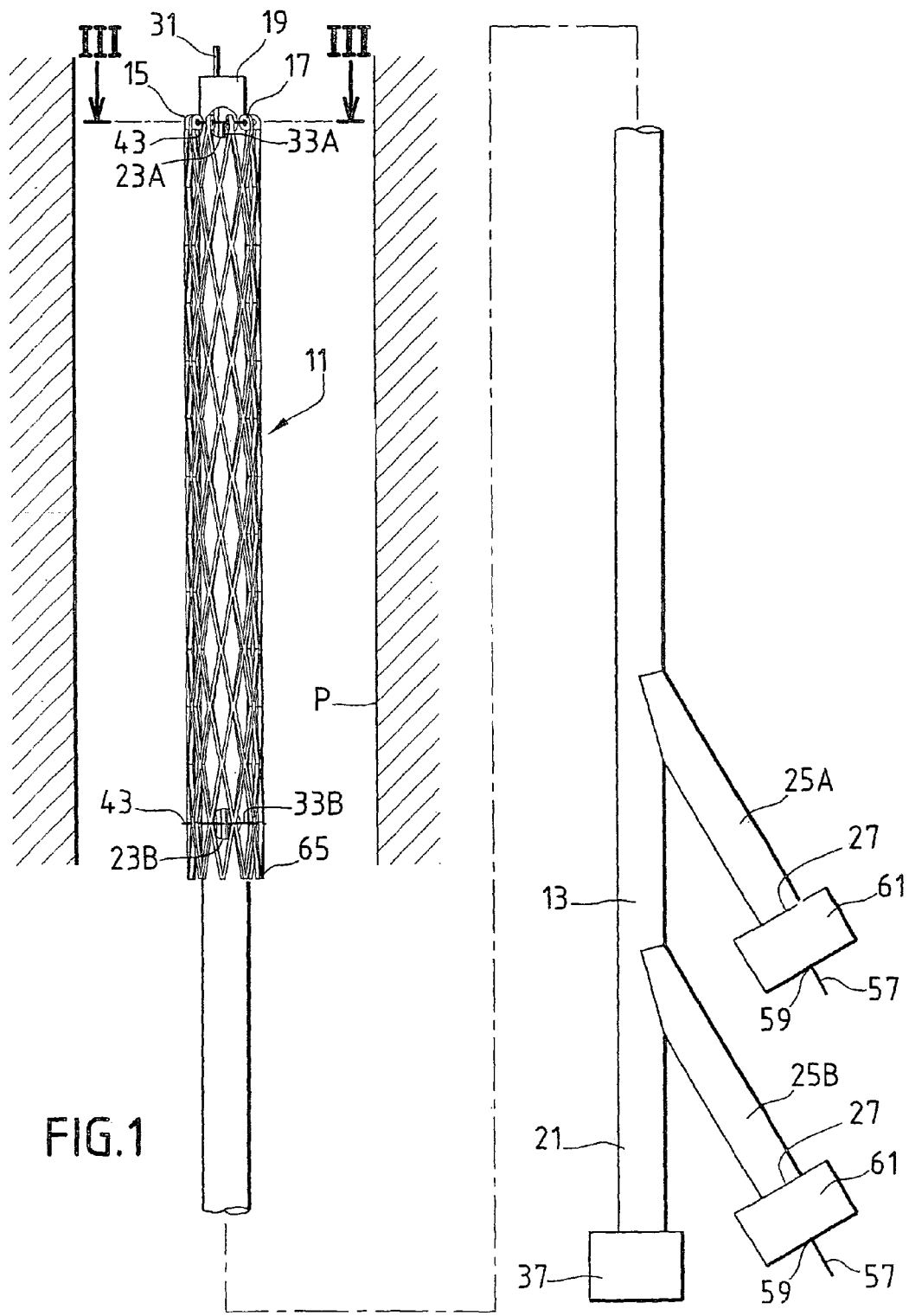
FIG. 1 is an elevation view of a first treatment device of the invention.
Figure 2:
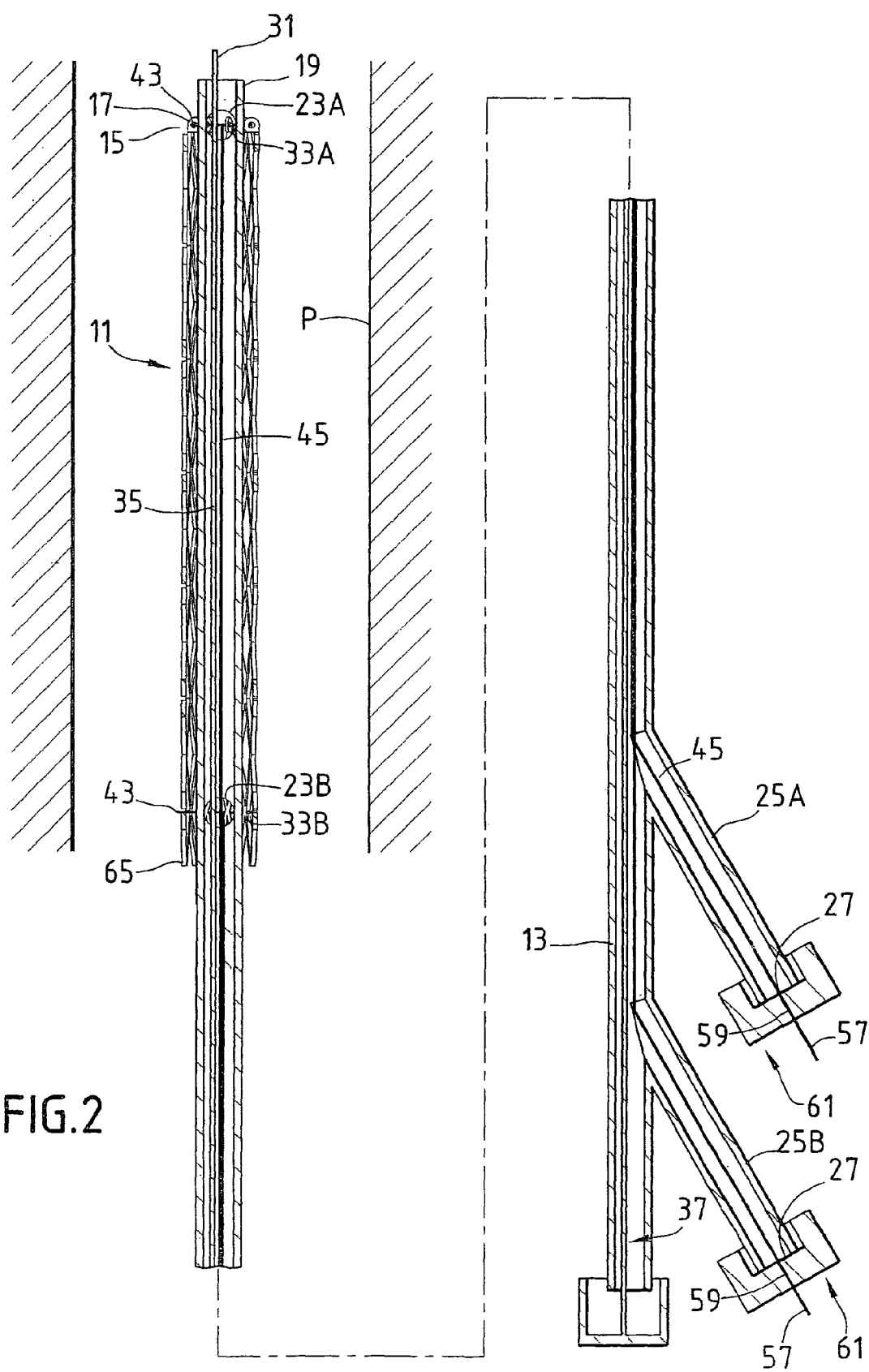
FIG. 2 is a section view on a longitudinal midplane of the FIG. 1 device.

In the embodiment shown in FIGS. 1 and 2, the prop 13 comprises a hollow flexible metal tube. The inside diameter of the tube is suitable for enabling the tube to be threaded onto a filamentary guide (not shown) installed in the patient, prior to putting the endoprosthesis 11 into place in a blood vessel of the patient.

The prop 13 extends longitudinally between a distal end 19 for implanting in the blood vessel and a proximal end 21 that is designed to be accessible to the surgeon.

Distal and proximal retaining openings 23A and 23B that are longitudinally offset are provided laterally in the prop 13. In this example, the openings 23A and 23B are formed on the same side relative to a longitudinal midplane of the prop 13. The distance between the distal retaining opening 23A and the proximal retaining opening 23B is substantially equal to the length of the endoprosthesis 11 when in its retracted state, length being measured in a longitudinal direction.

The prop 13 also has distal and proximal hollow branches 25A and 25B in the vicinity of its proximal end 21. These branches 25A and 25B are longitudinally offset along the prop 13 and communicate with the inside of the prop 13. A control passage 27 is formed at a free end of each branch 25A and 25B.

The releasable means for retaining the endoprosthesis 11 comprise a retaining rod 31 and distal and proximal retaining filaments 33A and 33B.

The retaining rod 31 is placed inside the prop 13. The length of the rod 31 is greater than or equal to the distance between the distal retaining opening 23A and the proximal end 21 of the prop 13. As shown in FIG. 2, the rod comprises an active portion 35 and an actuator prop 37.

The rod 31 is movable in translation inside the prop 13 between a retaining position in which the active portion 35 of the rod is in register with the two retaining openings 23A and 23B, an intermediate position in which the active portion 35 is in register with the proximal retaining opening 23B and is spaced apart from the distal retaining opening 23A, and a release position in which the active portion 35 is spaced apart from both retaining openings 23A and 23B.

Figure 3:
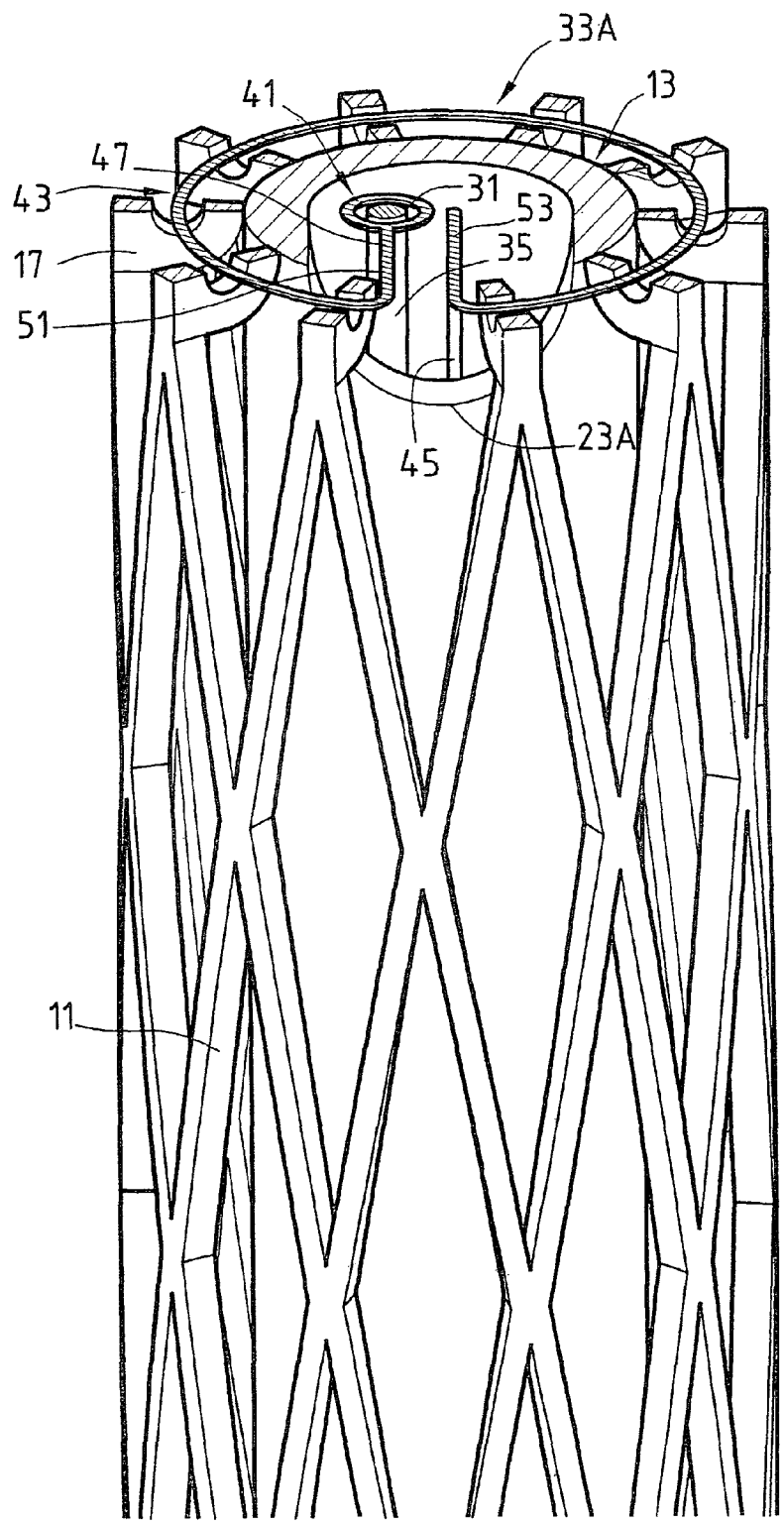
FIG. 3 is a fragmentary section on a transverse plane III-III showing a detail of FIG. 1.

In the embodiment shown in FIG. 3, the distal retaining filament 33A comprises a single strand which itself comprises an end eyelet 41, a tightening loop 43 and a control segment 45.

The end eyelet 41 is formed at a distal end of the strand. It is formed by a closed loop of small diameter. The active portion 35 of the rod 31 is engaged in the eyelet 41 while the rod 31 is in its retaining position.

The eyelet 41 is also deformable so that its width, when deformed, is substantially equal to twice the width of the strand. This width is less than the inside diameter of the loops 17.

The eyelet 41 is connected to the tightening loop 43 by a segment 47 engaged through the distal retaining opening 23A.

In the embodiment shown in FIG. 3, the tightening loop 43 is formed by a segment of strand engaged slidably in the end loops 17 of the trellis of the endoprosthesis 11, going around a circumference of the endoprosthesis 11, about a longitudinal axis.

The tightening loop 43 extends between a retaining end 51 connected to the eyelet 41 and a tightening end 53 connected to the control segment 45 and engaged in the retaining opening 23A. This tightening loop 43 fastens the endoprosthesis 11 to the prop 13 in the vicinity of the distal end 19 of the prop 13.

Furthermore, the active length of the tightening loop 43 can be varied so as to control deployment of the endoprosthesis 11 relative to the prop 13, as described below.

As shown in FIG. 2, the control segment 45 extends within the prop 13 between the distal retaining opening 23A and the control passage 27 in the distal control branch 25A of the prop 13.

A control end 57 of the control segment 45 is engaged through the control passage 27. Thus, a portion 59 of this segment projects beyond the branch 25A. The length of this projecting portion 59 can be varied and determines the length of the tightening loop 43.

Thus, an increase in the length of the projecting portion 59 causes the control segment 45 to move relative to the prop 13 towards the proximal end 21 of the prop, and also causes a corresponding decrease in the active length of the tightening loop 43, thereby tightening the endoprosthesis 11 against the prop 13 at the tightening loop 43.

When the endoprosthesis 11 is in its retracted state against the prop 13, the control segment 45 is in a position under tension.

Conversely, decreasing the length of the projecting portion 59 causes the control segment 45 to move relative to the prop 13 towards the distal end 19 of the prop, and also causes the active length of the tightening loop 43 to increase, and consequently causes the endoprosthesis 11 to be deployed away from the prop 13 at the tightening loop 43.

When the endoprosthesis 11 is in its expanded state, the control segment 45 is in a relaxed position.

An adjustment member 61 is placed bearing against the end wall of the branch 25A in register with the control passage 27. This member 61 has a central opening of adjustable diameter in which the projecting portion 59 is engaged.

By adjusting the diameter of the central opening in the adjustment member 61, the projecting portion 59 of the control segment 45 can be prevented from moving in selective manner relative to the prop 13, and the length of the projecting portion 59 can be determined, thereby determining the active length of the tightening loop 43.

Figure 4:
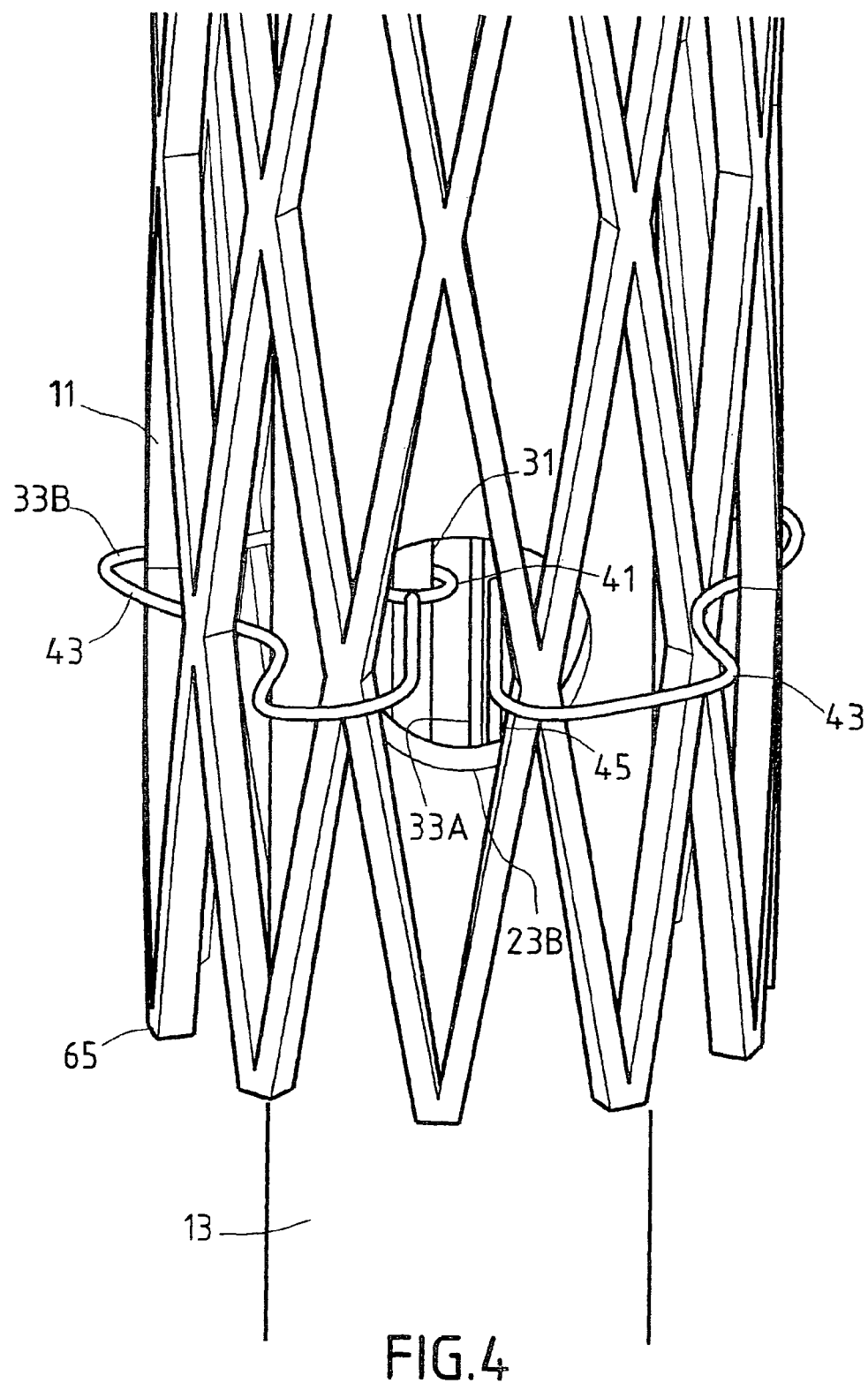
FIG. 4 shows another detail of FIG. 1.

As shown in FIG. 4, the structure of the proximal retaining filament 33B is analogous to that of the distal retaining filament 33A.

Nevertheless, unlike the distal retaining filament 33a, the tightening loop 43 is engaged in the trellis of the endoprosthesis 11 around a circumference, by passing successively inside and outside the trellis.

In a variant of this first device, the retaining openings 23A and 23B extend on opposite sides relative to a longitudinal midplane of the prop 13.

The operation of the first treatment device of the invention is described below by way of example.

Figure 5:
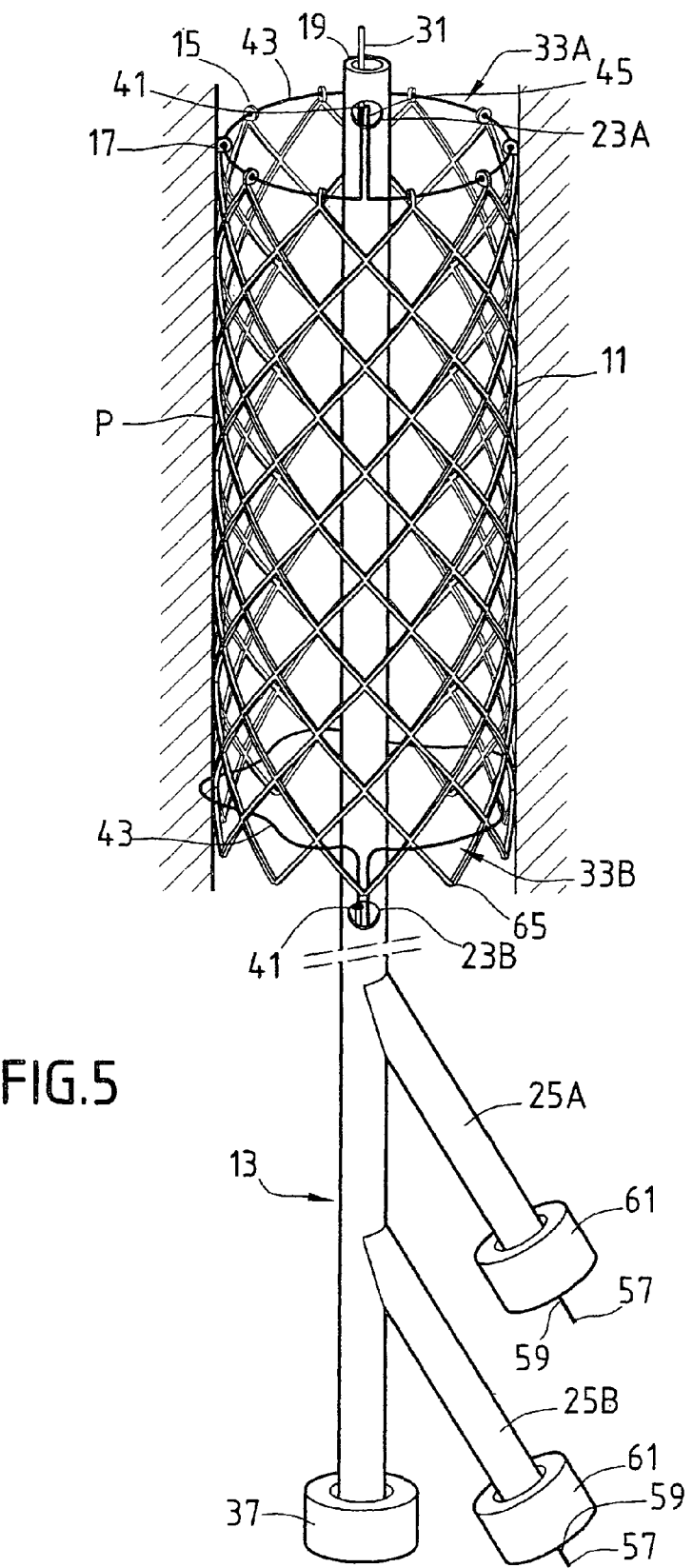
FIG. 5 is a view analogous to FIG. 1, with the endoprosthesis being deployed in reversible manner.

Initially, the device is kept in a package (not shown), with the endoprosthesis 11 in a deployed state analogous to that shown in FIG. 5.

In this configuration, the control rod 31 is in its retaining position. The distal and proximal retaining filaments 23A and 23B are engaged with the rod 31 and with the trellis of the endoproathesis 11.

This packaging conserves the mechanical properties of the endoprosthesis 11, particularly when the tubular trellis thereof is embedded in a flexible and leakproof film, e.g. an elastomer film.

Secondly, the surgeon extracts the device from its package. The guide (not shown) is put into place going along the blood vessel or the artery from an external point of insertion to the zone of the vein or the artery where the tubular endoprosthesis is to be implanted.

Thirdly, for the purpose of implanting the endoprosthesis 11 in the blood vessel or the vein, the surgeon actuates the adjustment member 61 on each retaining filament 23A and 23B so as to increase the length of the projecting portion 59 of the control segment 45. The control segment 45 is moved towards the proximal end 21 of the prop 13. The active length of the tightening loop 43 becomes shorter, so the endoprosthesis 11 is retraced against the prop 13 and is held securely relative to the prop 13.

The endoprosthesis 11 is then in its retracted state as shown in FIG. 1 with the trellis bearing substantially against the prop 13. It is in this condition that it is inserted up to the implantation position by being moved along the guide (not shown).

In some cases, in order to minimize radial size, a sheath (not shown) is placed around the endoprosthesis 11 prior to such insertion and is withdrawn once insertion has been performed.

Once the endoprosthesis 11 has been inserted, the surgeon proceeds to deploy it.

Depending on the shape of the vessel to be treated, the surgeon may decide to deploy one or the other one of the ends 15 and 65 of the endoprosthesis 11 first.

By way of example, the description below relates to deploying the distal end 15.

Firstly, the surgeon actuates the adjustment member 61 to decrease progressively the length of the projecting portion 59 of the control segment 45. The surgeon moves the control segment 45 towards the distal end 19 of the prop 13. Consequently, the active length of the tightening loop 43 increases.

The trellis of the endoprosthesis 11 then deforms spontaneously from the compressed state shown in FIG. 1 towards the deployed state shown in FIG. 5.

During this deformation, the end loops 17 of the trellis move away from the prop 13 and towards the walls P of the vessel that is to be treated, and they came to press against said walls P.

If the surgeon is not satisfied with the positioning of the distal end 15 of the endoprosthesis 11 when it is deployed, then the surgeon acts again on the adjustment member 61 to increase the length of the projecting portion 59, thereby reducing the active length of the tightening loop 43 so as to compress the endoprosthesis 11 back against the prop 13. The endoprosthesis 11 is then moved into a position that is more satisfactory.

In analogous manner, the surgeon subsequently deploys the proximal end 65 of the endoprosthesis by means of the proximal retaining filament 33B (FIG. 5).

It should be observed that the proximal end 65 and the distal end 15 of the endoprosthesis 11 are deployed in totally independent manner. Using the device of the invention, the surgeon can choose to deploy one and then the other one of the ends 65 and 19 of the endoprosthesis 11 in succession, or else to deploy both of them simultaneously, depending on the operating protocol.

Once the surgeon is satisfied that the distal end 15 of the endoprosthesis 11 is properly positioned, the retaining rod 31 is moved away from its retaining position to the intermediate position. During this movement, the eyelet 41 of the distal retaining filament 33A becomes separated from the rod 31.

Thereafter, the surgeon releases the control end 57 from the adjustment member 61 and pulls on the end 57 to bring the distal end of the distal retaining filament 23A to the control passage 27, successively via the loops 17 of the trellis of the endoprosthesis 11, the inside of the prop 13, and the control branch 25A.

The length of the path followed by the retaining filament 23A while it is being withdrawn is minimized so that the risk of this filament 23A becoming jammed in the prop 13 is reduced.

The distal end 15 of the endoprosthesis 11 is then fastened irreversibly against the walls P of the blood vessel.

The surgeon then verifies the positioning of the proximal end 65 of the endoprosthesis 11.

Once this proximal end 65 is positioned in satisfactory manner, the surgeon moves the rod 31 from the intermediate position to the release position, thereby releasing the eyelet 41 of the proximal retaining filament 33B.

Figure 6:
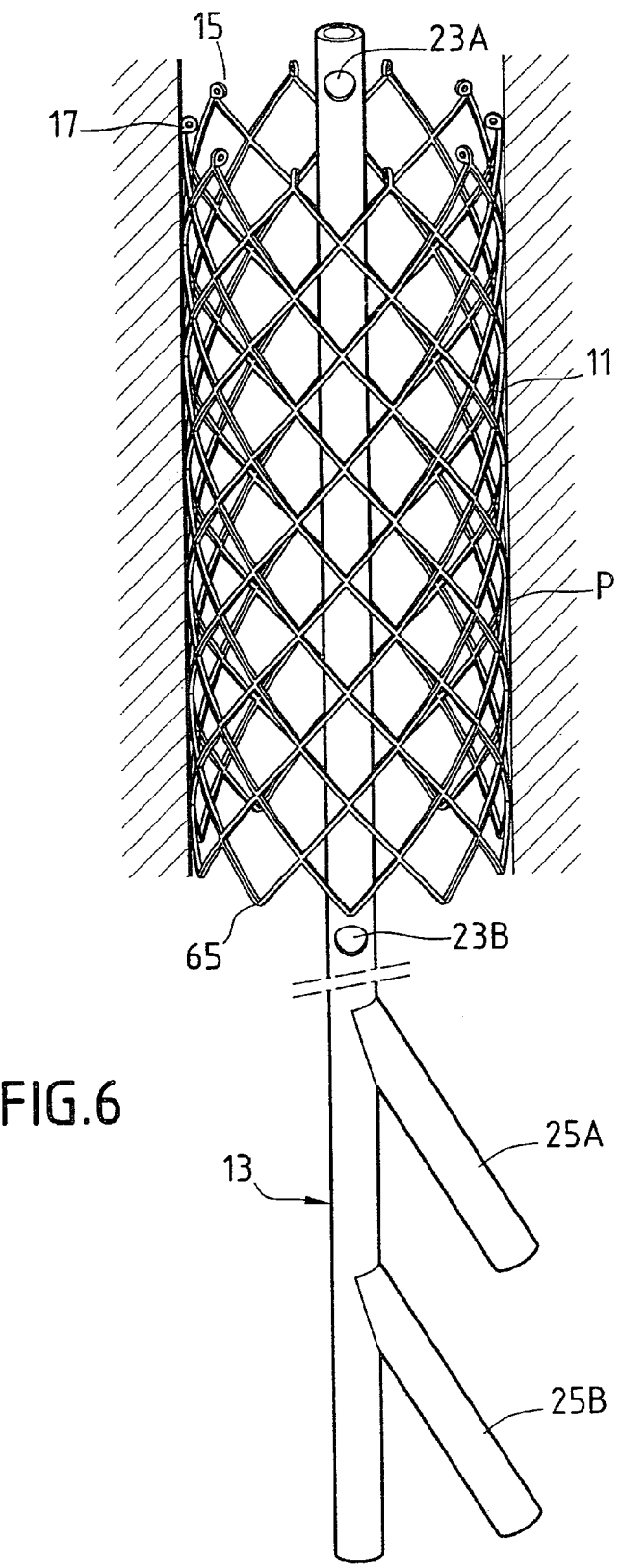
FIG. 6 is a view analogous to FIG. 5, in which the endoprosthesis is deployed in irreversible manner.

The surgeon withdraws the proximal retaining filament 33B as described above for the retaining filament 33A. The endoprosthesis 11 is pressed against the walls P of the blood vessel and the prop 13 is freed relative to the endoproathesis 11 (FIG. 6). It is then withdrawn from the blood vessel.

At this instant, the means for retaining the endoprosthesis 11 on the prop 13 have been fully withdrawn from the blood vessel.

Figure 7:
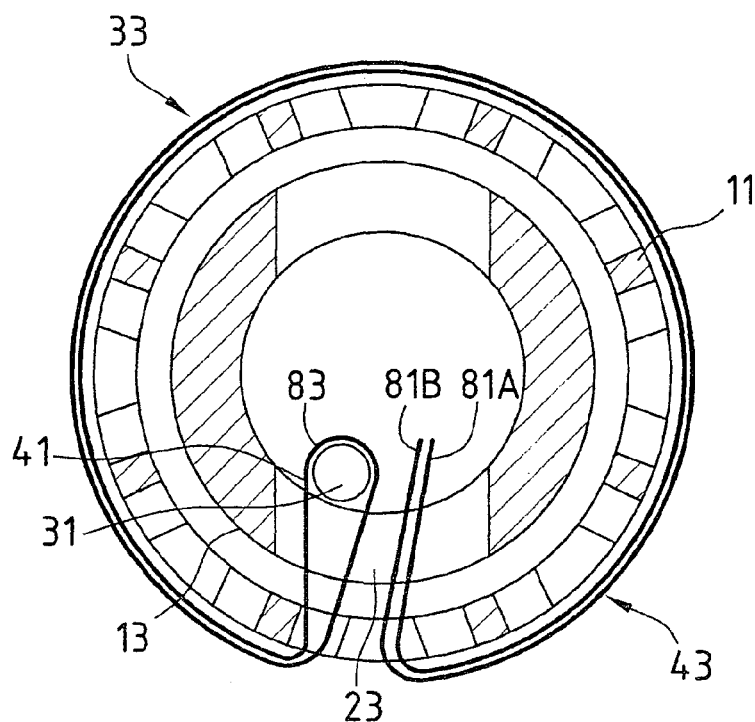
FIG. 7 is a fragmentary cross-section view of a second device of the invention.

Unlike the first device, the second device of the invention as shown in FIG. 7 comprises a retaining filament 33 having two parallel strands 81A and 81B interconnected at least by an end portion 83. The eyelet 41 is formed directly by the end portion 83 being engaged around the rod 13.

The tightening loop 43 extends around the endoprosthesis 11 outside the trellis of the endoprosthesis 11.

This configuration reduces the friction acting on the retaining filament 33 while it is being withdrawn.

Figure 8:
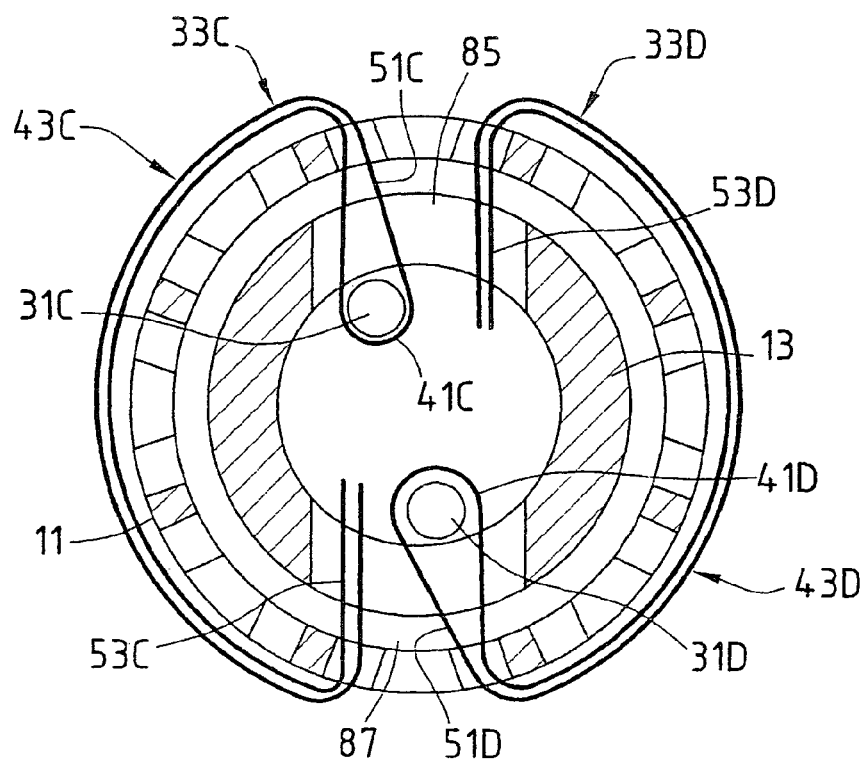
FIG. 8 is a fragmentary cross-section view of a third device of the invention.

A third device of the invention is shown in FIG. 8. Unlike the first device, the prop 13 has a retaining opening 85 and a tightening opening 87 that are distinct from each other, formed through the prop 13 in symmetrical manner about a midplane of the prop 13.

This embodiment further comprises, for each end of the endoprosthesis 11, first and second retaining filaments 33C and 33D associated respectively with first and second retaining rods 31C and 31D.

Each retaining filament 33C and 33D forms an eyelet 41C and 41D and a tightening loop 43C and 43D.

The retaining end 51C of the first tightening loop 43C is engaged in the retaining opening 85 and the tightening end 53C of the first tightening loop 43C is engaged in the tightening opening 87.

Thus, the first tightening loop 43C goes round the endoprosthesis 11 substantially over a first half of its perimeter and then intersects it on a transverse plane.

Conversely, the retaining end 51D of the second tightening loop 43D is engaged in the tightening opening 87 and the tightening end 53D of the second tightening loop 43D is engaged in the retaining opening 85.

Furthermore, the second tightening loop 43D surrounds the endoprosthesis 11 around the half of its perimeter that is complementary to the first half, the perimeter being taken in section on the same cross-section plane.

This device enables the two sides of the endoprosthesis 11 to be deployed independently on either side of a longitudinal midplane.

In a variant, two endoprostheses 11A and 11B can be mounted on a common prop, being offset longitudinally relative to each other. As shown in FIG. 9, the endoprostheses present an overlapping portion 101.

Each endoprosthesis 11A and 11B is also provided with independent retaining means 33A, 338, 33C, and 33D analogous to those of the first device. This device increases the accuracy with which one endoprosthesis is positioned relative to another. For this purpose, a first endoprosthesis 11A is positioned irreversibly in the manner described above and is released from the prop. The second endoprosthesis 11B is then positioned relative to the first endoprosthesis 11A by adjusting the length of the overlapping portion 101 as a function of the morphology of the vessel to be treated. Once the relative position of the two endoprostheses 11A and 11B is satisfactory, the second endoprosthesis 11B is released in turn in irreversible manner.

In another variant (not shown), the device may have two endoprostheses interconnected at one end so as to form a bifurcation. The prop also has a bifurcation separating the two branches on which each of the endoprostheses are mounted. Furthermore, each endoprosthesis is associated with a retaining rod and two releasable control filaments, as described above.

In another variant, the endoprosthesis may be disposed laterally on one side of the prop, the prop extending outside the duct defined by the endoprosthesis.

In another variant, each endoprosthesis can be fastened relative to the prop by a plurality of retaining filaments engaged in a corresponding plurality of retaining openings in the prop. Such a device enables the endoprosthesis to be released progressively in the vessel.

By means of the invention as described above, it is possible to have a device for treating a blood vessel which enables a tubular endoprosthesis to be deployed in a blood vessel in a manner that is initially reversible.

The device enables each end of the endoprosthesis to be released in succession, independently of each other.

Once the position of the endoprosthesis has been adjusted, the device enables the endoprosthesis to be released irreversibly leaving only the endoprosthesis in the blood vessel.

Furthermore, the structure of the device is particularly reliable because of its simplicity.

The device is also particularly compact because only one prop is used on which the endoprosthesis is mounted.

The device also applies to releasing endoprostheses that are extendible using a balloon, or to releasing distal protective filters.

The invention claimed is:

1. A device for treating a blood vessel, the device comprising:
   at least one tubular endoprosthesis that is deployable between a retracted state and an expanded state;
   a hollow prop which extends longitudinally between a proximal end of the prop and a distal end of the prop, the prop having at least one transverse retaining opening provided in a vicinity of the distal end;
   at least one releasable filamentary line forming at least one tightening loop which surrounds at least part of the endoprosthesis, the tightening loop extending through the retaining opening to an eyelet and being engaged through a tightening opening formed transversely in the prop, the filamentary line including a control segment which extends the tightening loop from the tightening opening, the control segment extending inside the prop at least to a control end of the control segment, the control end being actuatable from the proximal end of the prop; and
   at least one releasable retaining member, the eyelet being releasably engaged on the retaining member,
   wherein the control end includes a projecting portion which projects beyond the prop, a length of the projecting portion being movably adjustable,
   wherein the projecting portion is engaged in an adjustment member having a central opening, a diameter of the central opening being adjustable so as to control the length of the projecting portion with the eyelet being engaged around the retaining member, and
   wherein the control segment is arranged to be moveable relative to the prop towards the distal end of the prop so as to increase an active length of the tightening loop in response to the length of the projecting portion being movably decreased, and to be moveable relative to the prop towards the distal end of the prop from a position under tension in which the endoprosthesis is in the retracted state, to a relaxed position in which the endoprosthesis is in the expanded state, at least in the vicinity of the tightening loop.

2. A device according to claim 1, wherein the control segment is arranged so as to be displaceable relative to the prop towards the proximal end of the prop from the relaxed position to the position under tension.

3. A device according to claim 2, further comprising:
   a control passage formed in the prop in a vicinity of the proximal end, wherein the projecting portion is arranged to project beyond the prop through the control passage, and wherein the projecting portion is arranged such that the length of the projecting portion when the endoprosthesis is in the retracted state is greater than the length of the projecting portion when the endoprosthesis is in the expanded state.

4. A device according to claim 2, wherein the filamentary line comprises a single strand, the eyelet being deformable and being disposed at a distal end of the strand.

5. A device according to claim 2, wherein the tightening opening and the retaining opening are distinct, and wherein the at least one filamentary line comprises two filamentary lines forming two tightening loops, respectively, engaged in the tightening and retaining openings, the tightening loops extending on either side of a longitudinal midplane of the prop.

6. A device according to claim 2, wherein the retaining member comprises at least one retaining rod disposed to move inside the prop between a retaining position in which an active portion of the rod is in register with the retaining opening and the eyelet is engaged around the active portion, and a release position in which the active portion of the rod is spaced apart from the retaining opening, the rod including actuation means extending at least between the active portion of the rod and the proximal end of the prop in the retaining position.

7. A device according to claim 1, further comprising:
a control passage formed in the prop in a vicinity of the proximal end, wherein the projecting portion is arranged to project beyond the prop through the control passage, and wherein the projecting portion is arranged such that the length of the projecting portion when the endoprosthesis is in the retracted state is greater than the length of the projecting portion when the endoprosthesis is in the expanded state.

8. A device according to claim 7, wherein the filamentary line comprises a single strand, the eyelet being deformable and being disposed at a distal end of the strand.

9. A device according to claim 7, wherein the tightening opening and the retaining opening are distinct, and wherein the at least one filamentary line comprises two filamentary lines forming two tightening loops, respectively, engaged in the tightening and retaining openings, the tightening loops extending on either side of a longitudinal midplane of the prop.

10. A device according to claim 7, wherein the retaining member comprises at least one retaining rod disposed to move inside the prop between a retaining position in which an active portion of the rod is in register with the retaining opening and the eyelet is engaged around the active portion, and a release position in which the active portion of the rod is spaced apart from the retaining opening, the rod including actuation means extending at least between the active portion of the rod and the proximal end of the prop in the retaining position.

11. A device according to claim 1, wherein the filamentary line comprises a single strand, the eyelet being deformable and being disposed at a distal end of the strand.

12. A device according to claim 1, wherein the tightening opening and the retaining opening are distinct, and wherein the at least one filamentary line comprises two filamentary lines forming two tightening loops, respectively, engaged in the tightening and retaining openings, the tightening loops extending on either side of a longitudinal midplane of the prop.

13. A device according to claim 1, wherein the retaining member comprises at least one retaining rod disposed to move inside the prop between a retaining position in which an active portion of the rod is in register with the retaining opening and the eyelet is engaged around the active portion, and a release position in which the active portion of the rod is spaced apart from the retaining opening, the rod including actuation means extending at least between the active portion of the rod and the proximal end of the prop in the retaining position.

14. A device according to claim 1, wherein the prop comprises a single prop having at least two retaining openings that are longitudinally offset, a distance between the retaining openings being constant regardless of the state of the endoprosthesis.

15. A device according to claim 14, wherein a longitudinal distance between the two retaining openings is substantially equal to a length of the endoprosthesis while in the retracted state, measured in a longitudinal direction of the endoprosthesis.

16. A device according to claim 14, wherein the retaining openings extend on either side of a longitudinal midplane of the prop.

17. A device according to claim 14, wherein the at least one filamentary line comprises a filamentary line for each retaining opening, each control end being engaged in a distinct control passage formed in the prop in a vicinity of the proximal end.

18. A device for treating a blood vessel according to claim 1, wherein the at least one endoprosthesis comprises two endoprostheses that are longitudinally offset along the prop, each endoprosthesis being surrounded by at least one filamentary line associated with a retaining opening in the hollow prop.

19. A method of preparing a device according to claim 1 prior to being implanted in a blood vessel, the method being comprising:
conserving the endoprosthesis in the expanded state; and then
moving the control segment towards the proximal end of the prop so as to bring the endoprosthesis into the retracted state for implantation.

20. A device according to claim 1, wherein the hollow prop comprises a single prop having at least one distal retaining opening and at least one proximal retaining opening, wherein the at least one filamentary line comprises a proximal filamentary line and a distal filamentary line associated with the proximal retaining opening and the distal retaining opening, respectively, and wherein the at least one retaining member comprises a single retaining member arranged such that the eyelet of each filamentary line is engaged around the single retaining member.

21. A treatment method, comprising:
inserting a device into a blood vessel, the device including
at least one tubular endoprosthesis that is deployable between a retracted state and an expanded state,
a hollow prop which extends longitudinally between a proximal end of the prop and a distal end of the prop, the prop having at least one transverse retaining opening provided in a vicinity of the distal end,
at least one releasable filamentary line forming at least one tightening loop which surrounds at least part of the endoprosthesis, the tightening loop extending through the retaining opening to an eyelet and being engaged through a tightening opening formed transversely in the prop, the filamentary line including a control segment which extends the tightening loop from the tightening opening, the control segment extending inside the prop at least to a control end of the control segment, the control end being actuatable from the proximal end of the prop, and
at least one releasable retaining member, the eyelet being releasably engaged on the retaining member,
wherein the control end includes a projecting portion which projects beyond the prop, a length of the projecting portion being movably adjustable, and
wherein the control segment is arranged to be moveable relative to the prop towards the distal end of the prop so as to increase an active length of the tightening loop in response to the length of the projecting portion being movably decreased, and to be moveable relative to the prop towards the distal end of the prop from a position under tension in which the endoprosthesis is in the retracted state, to a relaxed position in which the endoprosthesis is in the expanded state, at least in the vicinity of the tightening loop, the device being inserted into the blood vessel with the length of the projecting portion of the control segment being at a maximum and the active length of the tightening loop being at a minimum;

after said inserting of the device, progressively decreasing the length of the projecting portion of the control segment so as to increase the active length of the tightening loop, the eyelet being engaged around the retaining member during said progressive decreasing of the length of the projecting portion; and thereafter moving the retaining member from a retaining position, in which the eyelet is engaged around the retaining member, to a release position, in which the eyelet is separated from the retaining member.

22. A treatment method according to claim 21, further comprising:

after said progressive decreasing of the length of the projecting portion and before said moving of the retaining member from the retaining position to the release position, increasing the length of the projecting portion of the control segment so as to decrease the active length of the tightening loop and compress the endoprosthesis against the prop; and thereafter adjusting a position of the device within the blood vessel.

23. A device for treating a blood vessel, the device comprising:

at least one tubular endoprosthesis that is deployable between a retracted state and an expanded state, the endoprosthesis comprising a trellis;

a hollow prop which extends longitudinally between a proximal end of the prop and a distal end of the prop, the prop having at least one transverse distal retaining opening provided in a vicinity of the distal end and at least one transverse proximal retaining opening provided in a vicinity of the proximal end;

at least one releasable distal filamentary line forming at least one distal tightening loop which surrounds at least part of the endoprosthesis, the distal tightening loop extending through the distal retaining opening to an eyelet and being engaged through a distal tightening opening formed transversely in the prop, the distal filamentary line including a control segment which extends the distal tightening loop from the distal tightening opening, the control segment extending inside the prop at least to a control end of the control segment, the control end being actuatable from the proximal end of the prop;

at least one releasable proximal filamentary line forming at least one proximal tightening loop which surrounds at least part of the endoprosthesis, the proximal tightening loop extending through the proximal retaining opening to an eyelet and being engaged through a proximal tightening opening formed transversely in the prop, the proximal filamentary line including a control segment which extends the proximal tightening loop from the proximal tightening opening, the control segment extending inside the prop at least to a control end of the control segment, the control end being actuatable from the proximal end of the prop; and at least one releasable retaining member, the eyelet of each filamentary line being releasably engaged on the at least one retaining member, wherein the proximal tightening loop of the proximal filamentary line weaves in and out of the trellis so as to be engaged with the trellis around a circumference of the endoprosthesis, and the distal tightening loop of the distal filamentary line is slidably engaged in end loops of the trellis so as to extend around the circumference of the endoprosthesis, wherein the control end of the distal filamentary line includes a projecting portion which projects beyond the prop, a length of the projecting portion of the distal filamentary line being movably adjustable, and wherein the control segment of the distal filamentary line is arranged to be moveable relative to the prop towards the distal end of the prop so as to increase an active length of the distal tightening loop of the distal filamentary line in response to the length of the projecting portion of the distal filamentary line being movably decreased, and to be moveable relative to the prop towards the distal end of the prop from a position under tension in which the endoprosthesis is in the retracted state, to a relaxed position in which the endoprosthesis is in the expanded state, at least in the vicinity of the distal tightening loop of the distal filamentary line.

24. A device according to claim 23, wherein the control end of the proximal filamentary line includes a projecting portion which projects beyond the prop, a length of the projecting portion of the proximal filamentary line being movably adjustable, and wherein the control segment of the proximal filamentary line is arranged to be moveable relative to the prop towards the distal end of the prop so as to increase an active length of the proximal tightening loop of the proximal filamentary line in response to the length of the projecting portion of the proximal filamentary line being movably decreased, and is arranged to be moveable relative to the prop towards the proximal end of the prop so as to decrease an active length of the proximal tightening loop of the proximal filamentary line in response to the length of the projecting portion of the proximal filamentary line being movably increased.

25. A device for treating a blood vessel, the device comprising:

at least one tubular endoprosthesis that is deployable between a retracted state and an expanded state;

a hollow prop which extends longitudinally between a proximal end of the prop and a distal end of the prop, the prop having at least one transverse distal retaining opening provided in a vicinity of the distal end and at least one transverse proximal retaining opening provided in a vicinity of the proximal end;

at least one releasable distal filamentary line forming at least one distal tightening loop which surrounds at least part of the endoprosthesis, the distal tightening loop extending through the distal retaining opening to an eyelet and being engaged through a distal tightening opening formed transversely in the prop, the distal filamentary line including a control segment which extends the distal tightening loop from the distal tightening opening, the control segment extending inside the prop at least to a control end of the control segment, the control end being actuatable from the proximal end of the prop;

at least one releasable proximal filamentary line forming at least one proximal tightening loop which surrounds at least part of the endoprosthesis, the proximal tightening loop extending through the proximal retaining opening to an eyelet and being engaged through a proximal tightening opening formed transversely in the prop, the proximal filamentary line including a control segment which extends the proximal tightening loop from the proximal tightening opening, the control segment extending inside the prop at least to a control end of the control segment, the control end being actuatable from the proximal end of the prop; and a single releasable retaining member, the eyelet of the distal filamentary line and the eyelet of the proximal filamentary line each being releasably engaged on the single retaining member, wherein the control end of the distal filamentary line includes a projecting portion which projects beyond the prop, a length of the projecting portion being movably adjustable, and wherein the control segment of the distal filamentary line is arranged to be moveable relative to the prop towards the distal end of the prop so as to increase an active length of the distal tightening loop of the distal filamentary line in response to the length of the projecting portion being movably decreased, and to be moveable relative to the prop towards the distal end of the prop from a position under tension in which the endoprosthesis is in the retracted state, to a relaxed position in which the endoprosthesis is in the expanded state, at least in the vicinity of the distal tightening loop of the distal filamentary line.

26. A device for treating a blood vessel, the device comprising:

at least one tubular endoprosthesis that is deployable between a retracted state and an expanded state;

a hollow prop which extends longitudinally between a proximal end of the prop and a distal end of the prop, the prop having at least one transverse retaining opening provided in a vicinity of the distal end;

at least one releasable filamentary line forming at least one tightening loop which surrounds at least part of the endoprosthesis, the tightening loop extending through the retaining opening to an eyelet and being engaged through a tightening opening formed transversely in the prop, the filamentary line including a control segment which extends the tightening loop from the tightening opening, the control segment extending inside the prop at least to a control end of the control segment, the control end being actuatable from the proximal end of the prop; and at least one releasable retaining member, the eyelet being releasably engaged on the retaining member, wherein the control end includes a projecting portion which projects beyond the prop, a length of the projecting portion being movably adjustable, and wherein the control segment is arranged to be moveable relative to the prop towards the distal end of the prop so as to increase an active length of the tightening loop in response to the length of the projecting portion being movably decreased, and to be moveable relative to the prop towards the distal end of the prop from a position under tension in which the endoprosthesis is in the retracted state, to a relaxed position in which the endoprosthesis is in the expanded state, at least in the vicinity of the tightening loop.

\* \* \* \* \*